(12) United States Patent
Sato et al.

(10) Patent No.: US 7,592,134 B2
(45) Date of Patent: Sep. 22, 2009

(54) VIRAL REDUCTION METHOD FOR PLASMA USING A LEUKOCYTE-REDUCTION FILTER AND TWO VIRUS-REDUCTION FILTERS OF DECREASING PORE DIAMETERS

(75) Inventors: Sakae Sato, Shizuoka (JP); Tetsuo Sato, Chofu (JP); Thierry Burnouf, Aubers (FR); Miryana Radosevich, Aubers (FR); Hadi Alphonse Goubran, Cairo (EG)

(73) Assignee: Asahi Kasei Medical Co., Ltd., Tokyo (JP)

( * ) Notice: Subject to any disclaimer, the term of this patent is extended or adjusted under 35 U.S.C. 154(b) by 278 days.

(21) Appl. No.: 10/531,570

(22) PCT Filed: Oct. 16, 2003

(86) PCT No.: PCT/JP03/13238

§ 371 (c)(1),
(2), (4) Date: Nov. 9, 2005

(87) PCT Pub. No.: WO2004/035066

PCT Pub. Date: Apr. 29, 2004

(65) Prior Publication Data

US 2006/0127874 A1      Jun. 15, 2006

(30) Foreign Application Priority Data

Oct. 16, 2002     (JP) ............................. 2002-301433

(51) Int. Cl.
*A01N 1/00* (2006.01)
*A61K 35/16* (2006.01)

(52) U.S. Cl. .......................................... 435/2; 424/530
(58) Field of Classification Search ...................... None
See application file for complete search history.

(56) References Cited

U.S. PATENT DOCUMENTS

| | | | |
|---|---|---|---|
| 6,190,855 B1 * | 2/2001 | Herman et al. | 435/2 |
| 6,797,169 B1 * | 9/2004 | Ide et al. | 210/500.27 |
| 6,861,001 B2 * | 3/2005 | Lee et al. | 210/651 |
| 6,867,285 B2 * | 3/2005 | Takahashi et al. | 530/382 |

FOREIGN PATENT DOCUMENTS

| | | |
|---|---|---|
| CA | 2 394 797 | 6/2001 |
| CN | 1249952 | 4/2000 |
| EP | 0 397 403 | 11/1990 |
| EP | 0 798 003 | 10/1997 |
| EP | 1 016 426 | 7/2000 |
| FR | 2 774 293 | 8/1999 |
| GB | 2 018 149 | 10/1979 |
| JP | 61-168367 | 7/1986 |
| JP | 63-68176 | 3/1988 |
| JP | 64-51075 | 2/1989 |
| JP | 1-192368 | 8/1989 |
| JP | 1-207240 | 8/1989 |
| JP | 1-254205 | 10/1989 |
| JP | 2-167232 | 6/1990 |
| JP | 3-146067 | 6/1991 |
| JP | 5-148150 | 6/1993 |
| JP | 2000-334037 | 12/2000 |
| JP | 2001-198214 | 7/2001 |
| JP | 2003-190276 | 7/2003 |
| WO | WO 92/04906 | 4/1992 |
| WO | WO 97/22245 | 6/1997 |
| WO | WO 01/14047 * | 3/2001 |
| WO | WO 01/45719 | 6/2001 |

OTHER PUBLICATIONS

Burnouf et al., "Nanofiltration of single plasma donations: feasibility study", Vox Sanguinis 84 : 111-119 (2003).*
English translation of JP-64-051075, pp. 1-33, 1989.*
English translation of JP-03-146067, pp. 1-23, 1991.*

* cited by examiner

*Primary Examiner*—Sandra E Saucier
(74) *Attorney, Agent, or Firm*—Young & Thompson

(57) ABSTRACT

The present invention relates to a plasma product or a serum product with an extremely low risk of viral contamination and a method for producing the same. Before treating plasma or serum to be used as a raw material for producing a plasma product or a serum product using a virus removal membrane, leucocytes contaminating the blood are removed. Thus, a plasma product or a serum product with an extremely low risk of viral contamination can be efficiently produced while preventing clogging. Since clogging scarcely arises, it is possible to carry out efficient filtration without applying an elevated pressure as the filtration proceeds.

11 Claims, No Drawings

VIRAL REDUCTION METHOD FOR PLASMA USING A LEUKOCYTE-REDUCTION FILTER AND TWO VIRUS-REDUCTION FILTERS OF DECREASING PORE DIAMETERS

TECHNICAL FIELD

The present invention relates to a human or animal plasma product or serum product which is highly safe, and to a method for producing the same.

BACKGROUND ART

Plasma or blood serum of humans or animals has a potential risk of being contaminated with viruses. Therefore, the possibility of being infected with high risk viruses such as the AIDS virus and various hepatitis viruses, in the case of humans, cannot be denied, if a blood product manufactured using plasma or serum as a raw material is used.

Methods for preventing viral infection involved in the use of these blood products have been proposed heretofore. For example, a chemical deactivating method using a surfactant or methylene blue has been known as a method for deactivating viruses in blood products. However, any of these methods has problems such as denaturation of proteins, requirements for complicated procedures for removing used chemical substances, and remaining of chemical substances in the finished products.

A method of removing viruses using a membrane, on the other hand, is excellent as compared with the other methods, because this method does not cause proteins to become denatured, is free from a substantial decrease in the activity, and can increase safety of the products against viruses. For example, Japanese Patent Application Laid-open Nos. 016837/1986 and 068176/1988 disclose methods for securing high safety against the hepatitis C virus or AIDS virus by treating plasma with porous hollow fiber having special performance.

Japanese Patent Application Laid-Open Nos. 192368/1989 and 254205/1989 disclose a filtration method and system using a filter membrane made of regenerated cellulose similarly. All these patent applications propose a method for removing viruses on the basis of size exclusion according to their size. On the other hand, Japanese Patent Application Laid-open No. 28581/1998 discloses a method for removing viruses under special conditions of a solution using a membrane having pores with a diameter larger than the size of the viruses.

Focusing attention on the fact that envelope viruses bond with LDL (low density lipoprotein), Japanese Patent Application Laid-open No. 334037/2000 proposes a method for removing the viruses using the membrane for removing LDL.

All these methods, however, have drawbacks. Patent documents 5 and 6 described above employ a method of removing viruses by utilizing exclusion or adsorption according to causing the viruses to aggregate under special conditions or causing them to bond with other mixtures. A problem with this method is the limitation to the type of viruses that can be removed. Another problem is an inconstant removing effect according to fluctuation of conditions.

On the other hand, Japanese Patent Application Laid-open Nos. 16837/1986 and 68176/1988 disclose methods for separating into viruses and proteins which have a smaller diameter than viruses depending on size thereof, the disclosed membranes is not necessarily satisfied about both virus removal ratio and protein permeating performance. Further, although the methods disclosed in Japanese Patent Application Laid-Open Nos. 192368/1989 and 254205/1989 are excellent with respect to viruses removal ratio, these methods cannot be applied in practical use due to the limited amount of proteins that can be treated.

DISCLOSURE OF THE INVENTION

An object of the present invention is to provide a safe and industrially effective method for producing a plasma product or a serum product by efficiently removing viruses from plasma or serum having a potential risk of virus contamination. Another object of the present invention is to provide the plasma product or serum product produced by the method.

As described above, a method for increasing safety against viruses without denaturing the proteins using a membrane has been studied, however, it has been difficult to provide a method of securing permeability of useful proteins and surely removing serious viruses since the plasma and serum contain a large amount of proteins, many of which are useful proteins with a high molecular weight.

The present inventors have conducted extensive studies to achieve the above objects and have found that viruses can be efficiently removed by introducing a step of removing leucocytes from human plasma or animal plasma used as a raw material before filtering the plasma through a virus removal membrane. As a result of further studies, the inventors have completed the present invention.

Therefore, the present invention relates to followings:

(1) A method for producing a human or animal plasma product or serum product comprising the following steps (a) and (b):
(a) a step of separating plasma from the whole blood originating from a human or animal and reducing leukocytes in the plasma and
(b) a step of filtering using a virus removal membrane after the step (a).

(2) A method for producing a human or animal plasma product or a serum product of comprising the following steps (a) and (b):
(a) a step of separating plasma from the whole blood originating from a human or animal immediately after collection of the blood and reducing leukocytes in the plasma immediately after the above separation and
(b) a step of filtering using a virus removal membrane after the step (a).

(3) The method described in (1) or (2) above, wherein the virus removal membrane used in step (b) has an average pore diameter of 100 nm or less.

(4) The method described in any one of (1) to (3) above, wherein the step (a) is a leukocyte-reducing step using a leukocyte removal membrane.

(5) The method described in any one of (1) to (4) above, wherein the steps (a) and (b) are carried out under the condition of a temperature of 25-40° C.

(6) The method described in any one of (1) to (5) above, wherein the steps (a) and (b) are carried out under condition of a pressure of 98 kPa or less.

(7) The method described in any one of (1) to (6) above, wherein the amounts of blood passing through in the steps (a) and (b) is 100-500 ml.

(8) The method described in any one of (1) to (7) above, wherein the treatment time for the step (b) is 10-40 minutes.

(9) The method described in any one of (1) to (8) above, wherein the virus removal membrane used in the step (b) has an average pore diameter of 75 nm or less.

(10) The method described in any one of (1) to (9) above, wherein the virus removal membrane used in the step (b) is a combination of a virus removal membrane having an average pore diameter of 75 nm and another virus removal membrane having an average pore diameter of 35 nm subsequent to the former membrane.

(11) A human or animal plasma product or serum product produced by a method comprising the following steps (a) and (b):

(a) a step of separating plasma from the whole blood originating from a human or animal and reducing leukocytes in the plasma and (b) a step of filtering using a virus removal membrane after the step (a).

BEST MODE FOR CARRYING OUT THE INVENTION

The present invention is based on the finding that viruses can be surely and efficiently removed, while ensuring permeability of useful components, by reducing leukocytes in advance in case of filtrating plasma before freezing to fresh frozen plasma using a virus removal membrane.

The present invention is also based on the finding that viruses can be surely and efficiently removed, by reducing leukocytes after firstly separating plasma from the whole blood, but not by removing leukocytes directly from whole blood.

The human or animal plasma or serum used as a raw material for producing the plasma product or serum product of the present invention is preferably a fresh raw plasma before freezing. Because plasma stored for a long time before freezing causes a reduction in permeability and in the permeated amount during filtration operation due to proteins, lipids, and the like that have bonded during storage, plasma with a short storage time before freezing is preferable.

Any method that can reduce leukocytes may be used in the leukocyte reducing step of the present invention. Among the methods, for example, a method of using ultracentrifugation can be given, but, a method of using a leukocyte removal membrane is preferable due to its simplicity. There are no specific limitations to the materials and the like of the leukocyte removal membrane in as much as the membrane can reduce leukocytes. For example, polyester nonwoven fabric can be used preferably.

The virus removal membrane used in the present invention refers to a membrane having at least a function of separating into viruses and proteins depending on the difference in the size. The virus removal membrane may be made of any material such as regenerated cellulose, polyethylene, polyvinylidene fluoride, and the like, with regenerated cellulose being preferable due to a low protein adsorption.

Although there is no unified method and criteria for defining the average pore size of various virus removal membranes used conventionally, the average pore size of the virus removal membrane can be defined in the present invention according to the virus removal performance as follows.

Specifically, a virus removal membrane with an average pore size of A nm refers to a membrane that can efficiently remove viruses with a particle diameter of A nm or larger. The above term "efficiently remove" refers to a logarithmic removal ratio (LRV=-$\log_{10}$ (virus concentration after filtration/virus concentration before filtration)) of 3 or more, preferably 4 or more, and more preferably 6 or more. For instance, a virus removal membrane with an average pore size of 100 nm refers to a membrane that can efficiently remove viruses with a particle diameter of 100 nm or larger.

Therefore, the virus removal membrane to be used is selected according to the average particle diameter of the viruses to be removed. For example, specific viruses to be removed by a virus removal membrane having an average pore size of 100 nm include the AIDS virus (HIV, average particle diameter: 100-120 nm), pseudorabies virus (PSR, average particle diameter: 120-200 nm), mouse leukemia virus (MuLV, average particle diameter: 120-150 nm), and the like.

In order to remove the AIDS virus (HIV) from plasma or serum, a virus removal membrane having an average pore size of 100 nm or less is useful. A virus removal membrane with an average pore size of 75 nm or less may preferably reduce the possibility of AIDS virus contamination and further remove even viruses with a particle diameter of 75-100 nm, thereby increasing the safety of the resulting product.

Protein permeability is so preferable that it is high as much as possible. The total protein permeability is preferably 70% or more, and more preferably 80% or more.

The virus removal membrane can also remove pathogenic factors and unnecessary impurities in plasma, if an appropriate pore size is selected.

The present invention provides a method for producing highly safe plasma from fresh plasma, comprising (a) a step of reducing leukocytes by using a leukocyte removal membrane and the like and (b) a step of removing viruses by filtering using a virus removal membrane after the step (a). Although these steps may be carried out using any apparatus and operation, reproducibility of the operation results can be expected and the quality of plasma after filtration can preferably be stabilized, if the operation is carried out using an atmosphere having (i) a temperature controlling means and (ii) a pressure-applying means under atmosphere-controllable conditions.

The temperature controlled by the temperature controlling means (i) may be any temperature at which the proteins are not denatured, with a preferable temperature range being from 25 to 45° C. If the temperature during filtration is less than 25° C., it takes a long time for filtration due to an increase in the plasma viscosity. It is difficult to treat within a practically acceptable time. Therefore, a filter temperature of 25° C. or more is preferable. If the treatment temperature is higher than 45° C., on the other hand, quality of proteins may unpreferably deteriorate due to heat. A more preferable temperature range is 30 to 37° C.

Although any pressure less than withstand pressure of the membrane may be applied during the treatment, pressure of 98 KPa or less is preferable to minimize protein denaturing, with a more preferable pressure being 80 KPa or less.

When separating plasma from the whole blood originating from human or animal in the present invention, it is preferable to separate immediately. The term "immediately" refers to a period of time in which the permeability of the membrane is not decreased due to coagulation or the like of proteins in the plasma. It is usually four hours or less, preferably two hours or less, more preferably one hour or less, and most preferably 10 minutes or less.

Although there are no specific limitations to the amount of plasma treated at one treatment, 100 to 500 ml is usually preferable, because the amount of plasma collectible at one treatment from a single donor is usually 100 to 500 ml. A treatment amount of less than 100 ml at one treatment is unpreferably not economical, whereas an amount of more than 500 ml imposes too great burden on the donor for collecting the plasma from the individual. A more preferable amount is 200 to 400 ml.

The treating time is determined depending on the amount of treated plasma, the membrane area, and the like and is preferably set 40 minutes or less. When the blood is filtered simultaneously with collection, the treating time of 40 minutes or less imposes only a little burden on the donor as an individual. If the filtration time is too long, it may cause denaturing of the resulting product, in some situations.

When plasma reduced leukocytes by the operation described above is filtered using a virus removal membrane with a pore size of 75 nm, followed by filtering using a virus removal membrane with a pore size of 35 nm, dangerous viruses such as the hepatitis C virus (HCV, average particle diameter: 30-60 nm) are removed, and a plasma product which has higher safety can be provided.

Serum obtained by previously removing fibrinogen from plasma can also be used as a raw material. A highly safe serum product can also be produced by removing fibrinogen in any step in the plasma product production.

EXAMPLES

The present invention will be described in more detail by examples.

Example 1

Immediately after separating plasma from a donor's blood using a plasma separation collection apparatus (AF104 manufactured by Fresenius), the separated plasma was filtrated through a leukocyte removal membrane ("Sepacell" manufactured by Asahi Kasei Corporation), followed by a virus removal membrane ("Planova" manufactured by Asahi Kasei Corporation) The "Planova" used had a membrane area of 0.06 m$^2$. The filtration is carried out first using a virus removal membrane with an average pore size of 75 nm, subsequently using a virus removal membrane with an average pore size of 35 nm. The filtration was performed at a constant flow rate using an OT-601 pump manufactured by JMS Co., Ltd. The filtration temperature was controlled at 35° C.±2° C.

250 ml of plasma was treated in 30 minutes under a pressure of 0.3 to 0.6 kg/cm$^2$. The amount of permeated protein is shown in Table 1. It can be seen from Table 1 that the amount of the permeated protein after filtration through the virus removal membrane with an average pore size of 75 nm was 75% or more, and that the amount of the permeated globulin and albumin is 90% or more and F-VIII 50% or more after filtration through the virus removal membrane with an average pore size of 35 nm, indicating no problems in practical use.

Comparative Example 1

An experiment was carried out in the same manner as in Example 1 except for omitting filtration using the leukocyte removal membrane (Sepacell) and filtration using the virus removal membrane (Planova) with an average pore size of 75 nm. Filtration was started using a Planova with an average pore size of 35 nm and a membrane area of 0.06 m$^2$. When 50 ml of the sample was filtered thereafter, the pressure increased to more than 1.0 kg/cm$^2$ and the operation was thus discontinued.

TABLE 1

| | Leukocyte removal | Virus removal membrane | |
| --- | --- | --- | --- |
| Protein | membrane | 75 nm | 35 nm |
| F-VIII | 88% | 75% | 55% |
| Globulin | 93% | 90% | 82% |
| Albumin | 100% | 100% | 100% |

Comparative Example 2

A whole-blood solution was collected and an anticoagulant was added, immediately followed by storing at 4° C. for two hours. After removing leukocytes using a leukocyte removal membrane (Sepacell, manufactured by Asahi Kasei Corporation), plasma was separated by centrifuging.

The separated plasma was filtered through the virus removal membrane Planova with an average pore size of 75 nm and a membrane area of 0.06 m$^2$ under the same conditions as in Example 1 at an initial pressure of 0.3 kg/cm$^2$. Since the pressure increased to more than 1.0 kg/cm$^2$ when 70 ml of the plasma was filtered, the operation was discontinued.

INDUSTRIAL APPLICABILITY

Since the safety against viruses of the plasma product or serum product obtained by the present invention is increased in accordance with the average pore diameter the virus removal membrane used for the filtration, the plasma product or serum product can be used for transfusion as is or can be preserved as frozen fresh plasma, and can be further used for transfusion or as a raw plasma for producing fractional (cut off) products.

The invention claimed is:

1. A method for reducing viruses from a human or animal plasma comprising the following steps (a) and (b):
   (a) separating plasma from whole blood obtained from a human or animal,
   reducing leukocytes in the plasma by filtering the plasma through a leukocyte reducing filter thereby producing leukocyte-reduced plasma,
   (b) filtering the leukocyte-reduced plasma through a first and second virus removal membrane which are in series and have decreasing average pore diameters,
   wherein the plasma has not been frozen prior to steps (a) or (b).

2. The method according to claim 1, wherein step (a) is performed within four hours after collection of the blood.

3. The method according to claim 2, wherein the step (a) is performed within two hours after collection of the blood.

4. The method according to claim 1, wherein the first virus removal membrane used in step (b) has an average pore diameter of 100 nm or less.

5. The method according to claim 1, wherein the steps (a) and (b) are carried out at a temperature of 25-40° C.

6. The method according to claim 1, wherein the steps (a) and (b) are carried out under a pressure of 98 kPa or less.

7. The method according to claim 1, wherein the amount of the blood in step (a) and the amount of leukocyte-reduced plasma in step (b) is 100 to 500 mls.

8. The method according to claim 1, wherein the duration of step (b) is 40 minutes or less.

9. The method according to claim 1, wherein the first virus removal membrane used in step (b) has an average pore diameter of 75 nm or less.

10. The method according to claim 1, wherein the first virus removal membrane used in step (b) has an average pore diameter of 75 nm and the second virus removal membrane has an average pore diameter of 35 nm.

11. The method according to claim 1, wherein in the step (a) the filtration is membrane filtration.

* * * * *

UNITED STATES PATENT AND TRADEMARK OFFICE
CERTIFICATE OF CORRECTION

PATENT NO. : 7,592,134 B2 Page 1 of 1
APPLICATION NO. : 10/531570
DATED : September 22, 2009
INVENTOR(S) : Sato et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 626 days.

Signed and Sealed this

Twenty-first Day of September, 2010

David J. Kappos
*Director of the United States Patent and Trademark Office*